(12) United States Patent
Joseph et al.

(10) Patent No.: US 6,441,375 B1
(45) Date of Patent: Aug. 27, 2002

(54) METHOD AND APPARATUS FOR AUTOMATED ON-LINE SUBSTRATE INDEPENDENT CALIBRATION AND MEASUREMENT SPECTRAL ANALYSIS

(75) Inventors: Gareth Joseph, Chippenham (GB); David F. Wood, Alfred, ME (US)

(73) Assignee: Eurotherm Gauging Systems, Inc., Billerica, MA (US)

( * ) Notice: Subject to any disclaimer, the term of this patent is extended or adjusted under 35 U.S.C. 154(b) by 0 days.

(21) Appl. No.: 09/477,699

(22) Filed: Jan. 6, 2000

(51) Int. Cl.$^7$ ................................................. G01J 5/02
(52) U.S. Cl. ........................... 250/339.09; 250/338.1
(58) Field of Search .................. 250/339.09, 338.1; 702/170, 172

(56) References Cited

U.S. PATENT DOCUMENTS

| | | | |
|---|---|---|---|
| 3,809,903 A | * 5/1974 | Cho et al. | 250/358 |
| 4,037,104 A | * 7/1977 | Allport | 250/359 |
| 5,235,192 A | 8/1993 | Chase et al. | 250/571 |
| 5,594,246 A | * 1/1997 | Sudo et al. | 250/310 |
| 5,900,633 A | * 5/1999 | Solomon et al. | 250/339.08 |

FOREIGN PATENT DOCUMENTS

| | | |
|---|---|---|
| DE | 198 20 948 C1 | 9/1999 |
| DE | 198 20948 C1 | 9/1999 |
| WO | WO 99/41590 | 8/1999 |

* cited by examiner

Primary Examiner—Georgia Epps
Assistant Examiner—M. Hasan
(74) Attorney, Agent, or Firm—Hamilton, Brook, Smith & Reynolds, P.C.

(57) ABSTRACT

The automated selection of the best calibration for measuring selected physical, chemical or atomic properties of continuous moving sheets, or of a coating on the sheets, is provided by the use of an on-line qualitative multi-band infrared measurement of the material. The multi-band qualitative measurement produces a spectral pattern of the material, which is matched to a library of potential materials. Once the best spectral pattern match is selected, then the known calibration constant values are used to make quantitative measurements on selected properties of the sheet of material, or of a coating on the material. Typically, a property of interest is the weight per unit area (i.e., grams per square meter) of a plastic coating on a paper substrate. The automated selection may be done on a periodic basis to adapt to variations in the substrate material that would otherwise cause the quantitative measurements of the coating to become erroneous due to calibration errors. Alternatively, the automated selection may be done whenever there is a splice in the substrate material, to catch substrate vendor changes, substrate composition changes or other substrate conditions which may affect calibration values. The automated selection may be done essentially continuously as a check on the quantitative measurements, in response to an alarm such as a quantitative measurement that is outside of a specified range, or in response to a manual operator instruction. With such an arrangement, a coating measurement becomes substrate independent and can maintain proper coating thickness process control over a wider product range, while permitting simpler inventory control.

41 Claims, 3 Drawing Sheets

METHOD AND APPARATUS FOR AUTOMATED ON-LINE SUBSTRATE INDEPENDENT CALIBRATION AND MEASUREMENT SPECTRAL ANALYSIS

BACKGROUND OF THE INVENTION

There are many examples of industrial fabrication processes that use a continuous moving sheet of material to improve the efficiency and reduce the cost of the final product. There are what are known as cast films, such as polycarbonate, extruded films, such as polyethylene, paper products, and various composite materials such as foil backed paper. There are also many industrial fabrication processes that use a continuous moving sheet of a substrate upon which one or more coatings are applied. Examples, of coated materials include waxed paper, polyethylene coated cardboard, and polarized films.

In each of the above noted manufacturing situations there are process control values that must be maintained in order to efficiently make the desired final product. An example of such a process control is maintaining a specified range of thickness for a plastic coating on a fibrous substrate for waterproofing. The plastic film, for example polyethylene, must be of sufficient thickness to have high integrity, but must be thin enough to be cost and weight effective. Therefore, it is known to use infrared (i.e., IR) spectrometry to measure the thickness of the plastic layer by means of measuring either the transmitted or the reflected intensity and computing a measure of relative intensity such as transmission, reflection or absorption of known IR peaks. The calibration constants developed from using these known IR peak intensities on samples of the same material composition of known thickness may then be used to make quantitative measurements on a material as the material is being manufactured.

A problem with this method is that the intensity value of the peak depends in art upon the composition of the substrate material, and so the calibration standards and constants are based upon a specific substrate composition. The substrate material may be a liquid base material for cast films, a sheet material for coating operations, or a solid material to which a material property transformation will take place during the manufacturing process. If the substrate composition changes, either because of a lack of process control at the substrate manufacturer, or because of a change in substrate source during a substrate roll splice, or even a change in humidity under which the substrate was stored, then the apparent thickness of the coating material may change because the calibrated intensity peak may now be different. It may also occur that even the same composition substrate material may have different IR intensity values when manufactured in different plants and under differing conditions. Thus it would be ideal to require that the rolls of the substrate composition that are spliced together during the coating process to provide the substantially continuous moving sheet of substrate material being coated, all be selected from a single manufacturer in order to minimize the calibration problem. However, this practice may present a warehousing and inventory supply problem, and may thus result in reduced efficiency manufacturing.

A similar problem exists in cast film manufacturing where a change in, for example, the molecular weight of a feed stock material may cause the calibrated value for an IR spectrometer reading of the continuous output sheet of dry film to drift, resulting in an incorrect reading, a consequent on-line change in some processing parameter such as casting speed in an attempt to fix the incorrect thickness, and a resulting incorrectly manufactured actual film thickness. Such problems in both coating and cast film manufacturing processes may result in factories that produce defective products for long periods of time, i.e., an entire day, resulting in financial loss.

As noted above, the calibration standard and constants used must be selected based upon the specific base or substrate material, and upon the coating material. Thus a processing line that manufactures plastic coating on paper products may require new calibration constants when the product being made changes, with consequent opportunity for lost time, increased work load and error potential. For example, in manufacturing plastic coatings on a matte finish paper, a specific set of calibration constants will have been determined and used. When manufacturing an otherwise identical product that coats the same plastic thickness on a shiny slick (as opposed to matte finish) paper substrate, the correct calibration may be different. The calibration constants may even have to change while using a single type of paper finish if the brightness of the printed color on the paper changes, such as may occur when the printing press reservoirs run low. It would improve manufacturing efficiency and reduce potential defective product to have an automatic method of adjusting calibration.

In many continuous moving sheet types of manufacturing processes, it is not sufficient to only measure the property of interest at a single point on the material. There is a benefit in making periodic measurements during manufacturing since the process parameters may change with time. There may also be a need to measure the property of interest at various points across the sheet width to account for spatial variation. In each one of these situations it is possible that the calibration values may have to change as the substrate composition changes in order to obtain accurate physical property values, i.e., for example thickness from the spectrometer readings. This is not possible using the present method of basing the measurements on a single set of calibration constants, or at best a limited number of sets, taken on a piece of the substrate material in a laboratory and applied thereafter for the entire manufacturing run of the particular material/substrate combination.

Another factor in the calibration problem is that the intensity at the wavelength peaks used to make the on-line quantitative measurements may be sensitive to slight variations in the substrate, such as differences in printed colors as previously noted, or differences in the amount of clay like material added to paper to increase the surface gloss and improve print quality. Substrate sensitivity also exists in the two wavelength ratio method. What is needed in the art is a substrate independent method of automatically selecting the correct set of calibration constants in order to accurately measure the property or characteristic of interest on a material.

SUMMARY OF THE INVENTION

A substrate independent method and computerized apparatus for on-line analysis of a continuous sheet of material is presented, using illumination of a material with a portion of the radiation spectrum. The method of measuring or evaluating a physical, chemical or atomic property, or characteristic, comprises the steps of using a qualitative analysis to determine the base material type, or select a set of calibration values, then using a quantitative analysis with the selected calibration to determine the value of the property or characteristic. The arrangement uses the entire spectrum portion in the measurement and not a few known absorption peaks. In a preferred embodiment of the invention, the spectrum used is in the infrared spectrum, but other radiation spectrums may also be beneficially used, such as x-ray, ultraviolet, Raman scattering radiation, or nuclear magnetic spin resonance radiation. A preferred detector is an IR spectrometer. First, a calibration is selected by using a radiation detector to measure the radiation intensity, absorbance or reflectivity, at each of a series of wavelengths scattered throughout the spectrum range. The measured intensity is used to calculate a spectral shape or pattern over the spectrum region. This measurement may be made either on a bare substrate, on a coated substrate or at both locations. The measured pattern is matched against stored spectral patterns of possible substrates in a spectral shape library, and the most closely matching spectral pattern is chosen. This qualitative spectrum identification of the substrate type selects the correct set of calibration standard values. Using the calibration values or constants, the same IR system and method may be used to make a quantitative measurement of a property, such as cure percentage, or film thickness, of the material at a variety of locations and times, depending on desired accuracy requirements. In general, the measured physical, chemical or atomic property or characteristic values will be stored in a memory and statistical calculations done. An alarm will be sent if the measured value exceeds a predetermined range, or if the qualitative match is not within a predetermined range.

In another embodiment of the invention, the measurement wavelengths will be evenly spaced to cover a preferred range of 1.3 to 3.4 microns, and the number of wavelengths used will be greater than 10 depending upon the accuracy desired for the spectrum pattern matching.

In still another embodiment of the invention, the pattern matching step is performed by a point by point comparison of the measured intensity at each wavelength versus the intensity of each of the stored spectral patterns at the respective wavelengths, calculating a difference value at each wavelength, and calculating the standard deviation for the difference values for each one of the library shapes. The best pattern match is the one with the lowest calculated standard deviation. Other methods of pattern or shape matching may be used including least squares comparisons, root mean square, correlation, etc.

In another embodiment of the invention, the measured physical property is the thickness of a coating on at least one side of the substrate material, and in another the substrate material is a composite material having multiple bonded layers, for example bonded fibrous material such as paper, or fibrous material having an inorganic or a metallic material coating.

In yet another embodiment of the invention, the selection of calibration value step is either performed after a coating has been applied to the substrate, or the calibration selection step is performed both prior to and after the coating. In another embodiment the calibration selection step is performed periodically, or at splice locations where rolls of feedstock are connected to form a continuous layer.

In still another embodiment of the invention, the quantitative physical property measurements are taken essentially continually over substantially the entire width of the continuous sheet of material.

In general, the arrangement comprises an automatic qualitative evaluation of which of a group of possible substrate spectral shapes is most similar to the measured spectral profile, and then using the selected calibration constants to make quantitative measurements of one or more material properties, such as thickness. With such an arrangement the periodic re-calibration of a process control measurement may avoid the errors caused by unannounced changes in the substrate, and process drift and out of specification waste material may be reduced.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
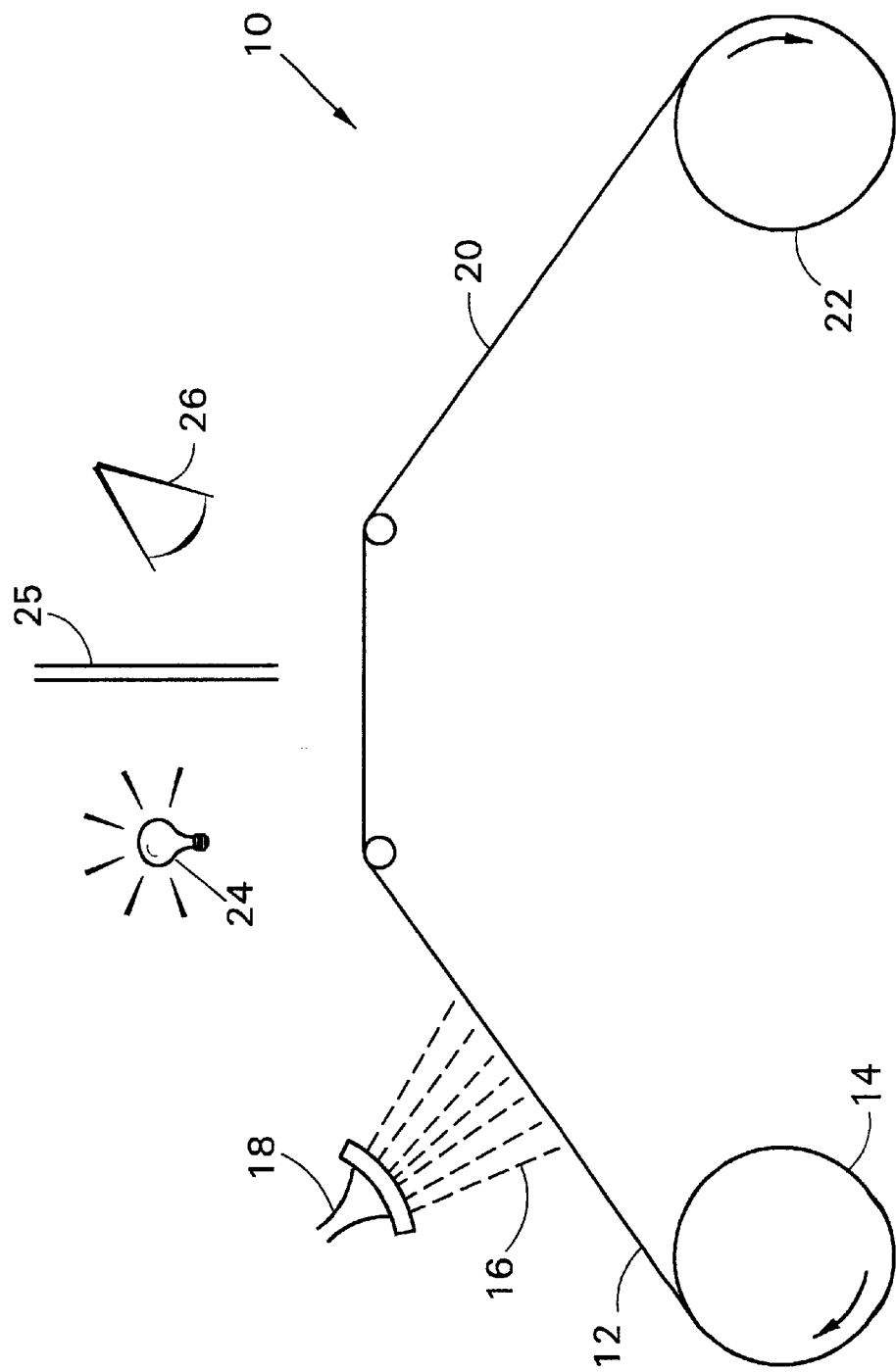
FIG. 1 shows a schematic of a continuous sheet process.

FIG. 1 shows an exemplary continuous sheet fabrication process apparatus 10 having a solid sheet substrate 12 supplied from a rotating roll of material 14. The substrate 12 may be typically supplied by any or all of a group of multiple suppliers who may be chosen based upon current quality, speed of delivery or price. To maintain continuous and uninterrupted timely raw material supply it is common to have multiple sources of base materials. Each supplier will have a slightly different composition of the substrate 12, even though all will likely be within the specification range for all properties of interest, such as molecular weight, weight per unit area (typically expressed as grams per square meter or GPM), surface specularity, etc. As a result of the variations within the specified ranges there will be consequent variations in the absorption spectrums measured on each different substrate even though all of the substrates are intended to be the same. In other situations the substrate material may be changed to make a different product with the same coating. If the change is erroneously unannounced the measurement may be out of specification and the line will stop. This is another situation where automatic selection of calibration constants will improve manufacturing efficiency. In addition, certain types of substrate materials, such as paper, will have differing amounts of absorbed water vapor depending upon the storage conditions and times, weather and other environmental issues. Moisture levels may also affect the substrate spectrum shape in certain material compositions.

In this exemplary manufacturing process the uncoated substrate 12, for example paper, is coated with a material 16, such as a plastic coating to water proof the paper, via a spray head apparatus 18. There are other well known methods for coating substrates including extrusion skim coating, lamination of a dry film, evaporation and chemical vapor deposition, to which the principles of the present invention may be applied. In the present example, the liquid material 16 may be baked or air dried to produce the final coated film 20, which is rolled up on a rotating drum 22.

Typically, a coating process such as that illustrated in FIG. 1 will have some method of controlling the thickness of the coating material 16. For example, if the coating 16 is too thick, then the amount of material sprayed per unit time from nozzle 18 may be reduced to bring the final coating thickness back into the specified range. In a typical high production process, the control of the coating thickness must respond quickly to any measured variation in coating thickness to avoid having an excessive amount of final product produced which is not within the specified values. Therefore it is typical to have some form of on-line measuring method that can be calibrated against known standards to provide such a quick response to thickness (or other physical, chemical or atomic property) change in the manufacturing process 10.

It should also be noted that the material 12 may not be supplied by an external supplier, and may also be formed in the same manufacturing line 10 as the coating. Further material 12 need not be a solid but may also be an extruded or a cast film of plastic or metal. Also note that the illustrated spray coating is not required, and the second material 14 may be another solid sheet of material like material 12, the indicated process 10 may be the lamination of the two sheets into a composite material. The principles of the invention apply in any of the well known manufacturing processes that require on going physical property measurements of long sheets.

A known method of measuring various physical properties of many materials, especially clear dielectric films such as plastic, is to examine the magnitude of known absorption peaks of transmitted or reflected light. In FIG. 1 a source of light radiation 24 is shown illuminating the layer of material. It should be noted that the principle of the present invention also apply to other forms of radiation that have a different spectrum of wavelengths or energies. In a preferred embodiment of the present invention, the radiation source 24 emits a broadband of frequencies in the IR region, having wavelengths preferably between 1.3 to 3.4 microns. Radiation from source 24 travels to the film 20 (which is a coated film in this illustrative example) and is typically reflected to detector 26. Optically dense barrier 25 may be used to prevent direct illumination of detector 26. In a preferred embodiment of the present invention, the source 24 and detector 26 are combined in any of many well known types of infrared spectrometer. Note that the position of source 24 could be shown to be below film 20, with the radiation passing through film 20 to reach detector 26, thus illustrating the transmitted radiation absorption spectrum case. Similarly, the detector 26 may be positioned on the opposite side from the radiation source 24.

In either case discussed, the light received at the detector 26 may have a different spectral distribution of peaks and peak heights (known as a spectral pattern or shape) than the emitted radiation from source 24. This is because the material in film may absorb some particular wavelengths better than other wavelengths. The particular pattern of spectral peak location shifting is a known method of identifying materials. It is known in the art to use the height (or intensity) change in a known absorption peak of a particular material, to measure the thickness or some other physical property of the material. Such a method requires known calibration constants based on absorption changes measured on samples of known properties, such as a known thickness. It is also known in the art to use a ratio of two known peaks for a particular material to measure the physical, chemical or atomic property of interest.

A known problem with the previously discussed methods of measuring on-line physical properties is the sensitivity to small variations in the composition of the material 16, or of the substrate 12. As a result of this sensitivity it is necessary to have material responses measured and compared against known library standards as frequently as necessary to ensure that substrate changes do not alter the measurement enough to cause out of specification product. This requirement causes lost time and inefficient production, and is incompatible with what is known as just in time manufacturing since it does not allow for easy use of multiple vendors for raw material or substrates, nor does it allow easy shifting of product lines with changing order flows.

The present invention reduces the sensitivity of the spectrometer measurement to small raw material or substrate variations (such as different vendors for the same material) by providing an automated on-line method and apparatus for taking spectral measurements either on a periodic basis, or at a trigger event, such as a roll splice. The method uses a broad band of wavelengths rather than a single wavelength or ratio of two wavelengths to illuminate the sample, and automatically curve matches the resulting wave pattern to a library of possible calibration standards. Various matching methods may be used such as least squares, regression correlation or other well known methods. In a preferred embodiment of the invention the spectral shape matching is done by a point by point comparison and difference measurement at each of the selected wavelengths between the sample and each one of the library of calibration standards. The standard deviation of the differences at each wavelength is calculated for each library member, and the one having the least difference from the sample values is chosen for calibration.

Figure 2:
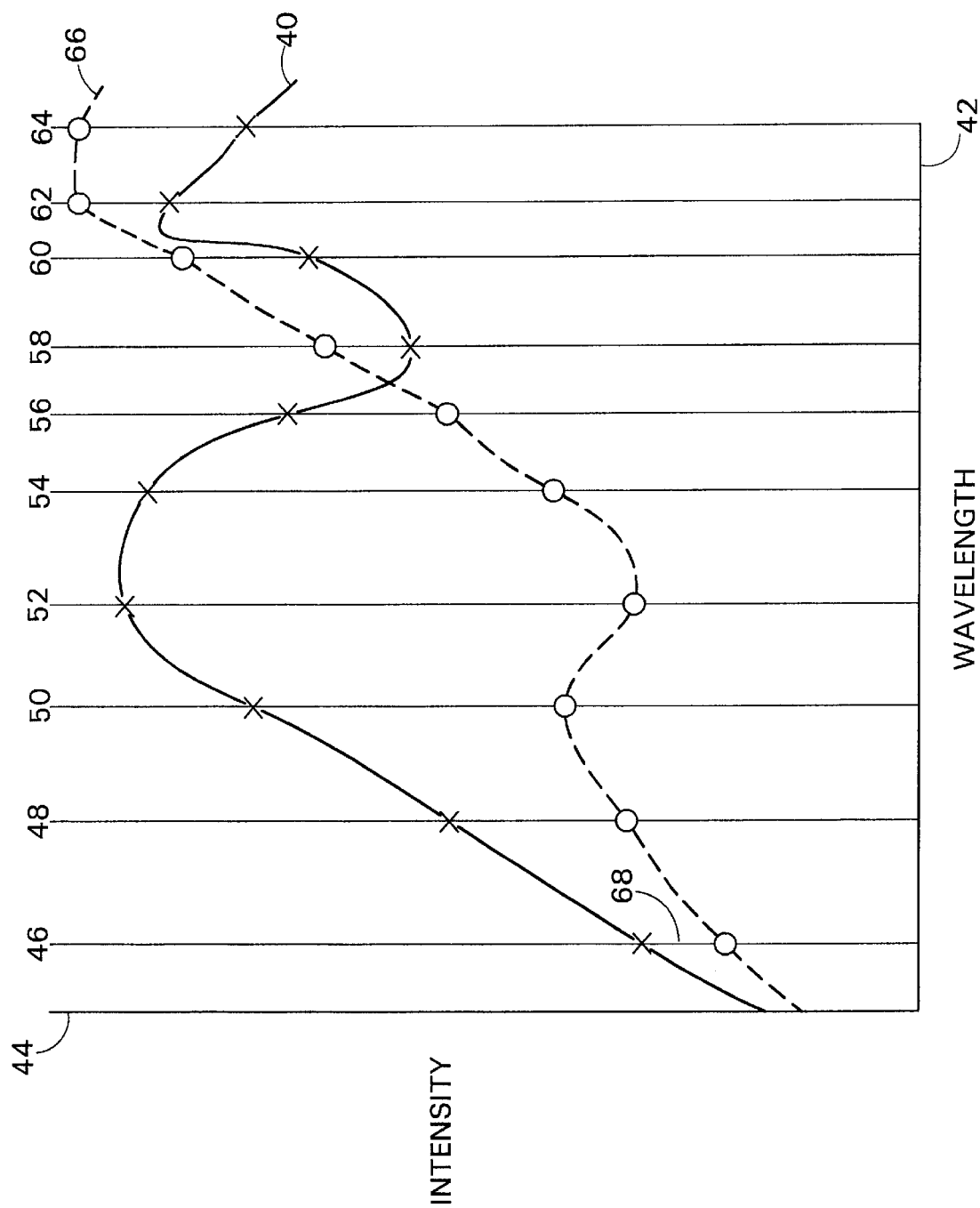
FIG. 2 shows spectral shape charts.

FIG. 2 shows how a measured spectral shape 40, shown as connected "X"s, having a horizontal axis 42, wavelength, and a vertical axis 44, relative intensity, is compared at each one of the ten selected wavelengths 46–64, to a library spectral shape curve 66 for a standard substrate, shown as connected "O"s. Note that the wavelengths are here shown to be non-evenly spread out over the spectral range, perhaps to take advantage of known strong absorption points, but this is not necessary to practice the invention. Also note that the number of wavelength points chosen for the analysis is not limited to ten or any other number, but will depend on how accurately the measured spectrum must be matched to the specific potential calibration standards in the library. The more similar the different potential library standards are for a given product, the larger the number of wavelength points that may be analyzed to assure a good match.

At each of the ten chosen wavelengths 46—64 there is a difference value between the sample curve 40 and the library curve 66. For example at wavelength 46 the difference between the two curve values is labeled 68. In this particular example, all of the individual differences, such as 68, for all of the wavelengths 46–64 will be added together and divided by ten to find an average difference value. The same procedure would be performed for each of the library curves and the library curve having the lowest average difference value would be selected as the curve that most closely matches the measured curve 40, and thus be used to select the calibration to use while making on-line quantitative measurements of the product. Note that this example uses a simple measure such as average difference value for simplicity. In a preferred embodiment the ten difference values would have the standard deviation calculated and used as the shape matching method. Many other well known statistical methods may also be employed, but experience has shown that the standard deviation method is adequate for some applications. The above described procedure is typically known as a qualitative analysis, since the result is the discovery of a difference in some type of quality (i.e., curve shape or pattern) between similar members of a set, not a quantitative measurement such as a number.

Figure 3:
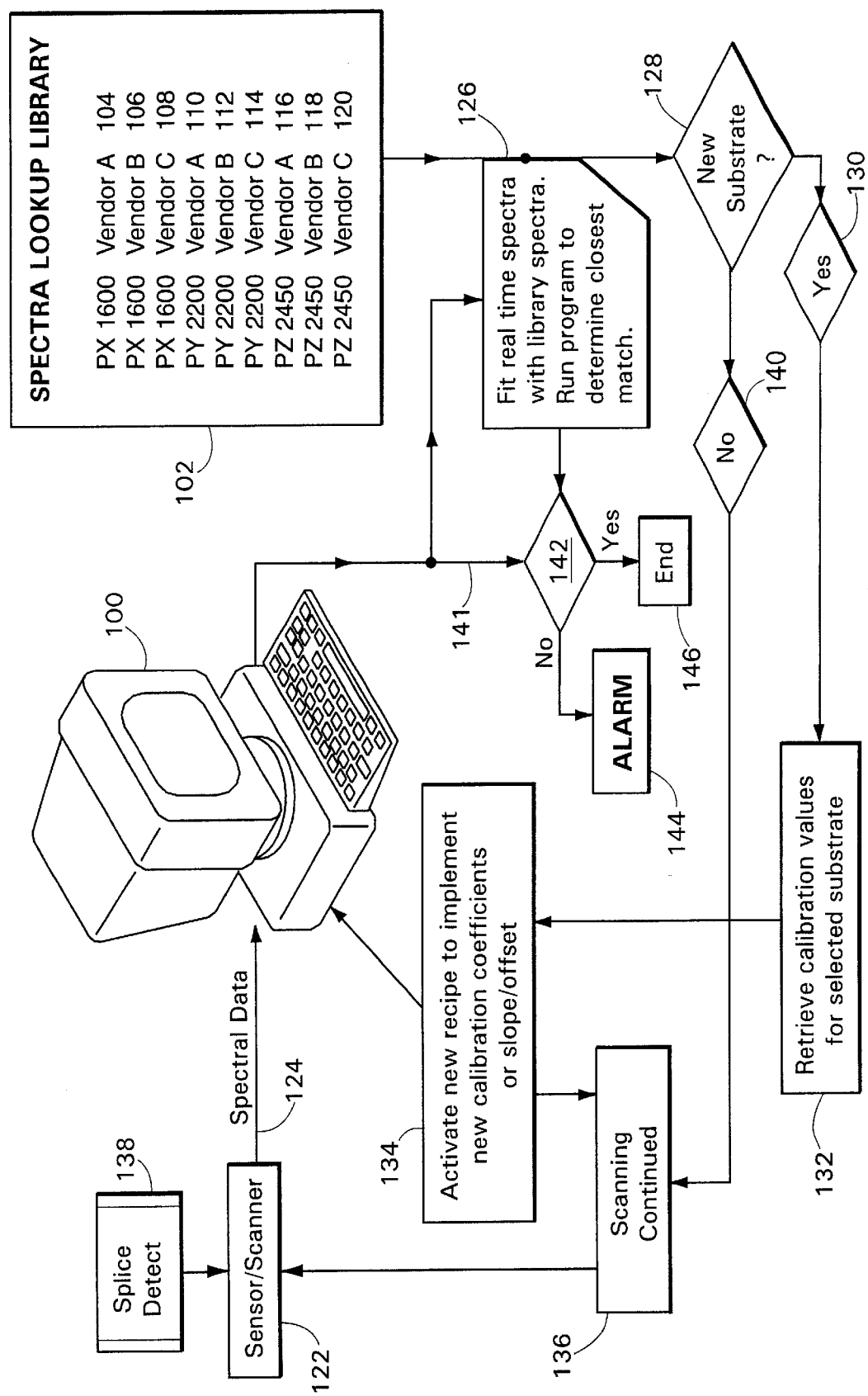
FIG. 3 shows a flowchart of a program to implement the invention.

FIG. 3 is a top level flowchart of a computer 100, controlling an illustrative process of coating a roll of material to be later cut up into individual units. The computer 100 has access to a memory with a library 102 of potential substrate compositions and spectral patterns of the substrates at various wavelength ranges. The illustration shows that for this product there are at present nine different groups 104–120, of three different type substrates, each type acquired from three different vendors. Each one of the nine different substrate possibilities, 104–120 has a stored spectral pattern such as that shown previously in the FIG. 2 example.

At the beginning of a production run the computer 100 will access the library 102 of potential calibrations appropriate to the materials being used. The sensor scanner 122 under the control of the computer 100 takes a real time spectral reading of either the raw material prior to coating, or the coated material, and sends the spectral data 124 to the computer 100. The computer 100 compares the spectral data 124 to each member of the library 102 to determine the closest curve match at step 126. If the selected substrate calibration is different from the previously selected calibration value, which is a certainty in the present case of an initial measurement, then the determination step 128 is determined to be yes at step 130 and the set of calibration constant values, i.e., such as slopes and offsets of the selected substrate, i.e., 104–120, are retrieved from a memory at step 132. The calibration values are inserted into the control portion of the computer 100 for use in the quantitative measurements in step 134 and scanning of the material undergoing the process is either begun or continued at step 136.

As the scanning of the material by scanner 122 continues, there may be a point where a new roll of substrate will be spliced onto the present roll to continue the processing. Such a splice presents the possibility that the new roll of substrate material may be of a different material, or be the correct material but from a different vendor than the previous roll. A splice detector 138, such as a capacitive thickness gauge, notes the change in overall gross substrate thickness at the splice and notifies the computer 100, which may preferentially be programmed to automatically re-select whenever a splice is detected, following the previously described procedure. Further, computer 100 may be beneficially programmed to preform a selection procedure at periodic intervals. In such a case, it is possible that at step 128, the answer is "no" there is no change from the previous substrate, and thus step 140 continues the scanning with no change.

The computer 100 also provides a curve fit threshold value 141 which is compared to the calculated spectral match of the measured data 124 to the library spectral curves 104–120 at program step 142. If all of the library spectral patterns are mismatched from the measured values 124 by a value greater than threshold 141, then step 142 answers no, and an alarm or flag is set at 144. If at least one of the library spectra 104–120 match the measured values 124 within the threshold limit 141, then step 142 is satisfied and the alarm subroutine ends at 146, until the next spectral matching program step 126 is run.

The computer 100 and the sensor/scanner 122 between re-selection procedures are preferably making quantitative measurements on the material being processed using the calibration constants provided by step 134. The quantitative measurements are sent to computer 100, which is preferably programmed to compare the measured data to a specified value for the production run, and to store and perform statistical calculations on the data. The statistical data may be used to form a point to point geographical map of the value of the quantitative data, for example a coating thickness, across the length and width of the sheet or layer of substrate material. The data may be used to provide a time dependent analysis of the quantity value, i.e., as the processing run proceeds. Both positional and temporal maps or profiles are beneficial to the control of manufacturing processes. The computer 100 may be programmed to either alert a user when the measured data exceeds a predetermined value range, or to directly adjust some part of the production process to return the measure value to within the specified range, or both.

The process of re-selection of the best fit set of calibration constant values may be beneficially initiated by the splice detector previously described, at periodic intervals as previously discussed, at every quantitative measurement, in response to a quantitative measurement that exceeds a specified range, in response to an alarm, by manual intervention of an operator, by various combinations of these methods, or initiated by other methods, such as continuously checking the qualitative curve fit and re-selection process. For example, if the quantitative measurements include measurements being made at locations across the width of a roll of material in an essentially continuous process, then an alarm may be set if any one of the quantitative readings is out of a specified range of values. Alternatively, an alarm may be set if some statistical measure, such as a running average of measured values, or the standard deviation of a running average exceeds a specified value contained in the computer 100. The alarm may be beneficially used to initiate the re-selection process to determine if a problem exists. Examples of reasons for manual operator intervention might include detection of power surges or blackouts, or other changes in the manufacturing environment such as the relative humidity.

It should also be noted that the curve matching step does not require that each and every one of the library spectral curves 104–120 be compared to the measured data 124. The comparison step 142 may be terminated if one of the library curves 104–120 is found to match the measured value 124 to within a specified value contained in computer 100.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of measuring a property of a moving material with a gauging system comprising the steps of:
   illuminating the moving material with multiple wavelengths of light;
   detecting light coming from the material with a detector;
   forming a measured spectral pattern for the material from the detected light;
   matching the measured spectral pattern with one of a plurality of spectral patterns stored in a spectral pattern library; and
   selecting a set of calibration values for said one of a plurality of spectral patterns from a calibration value library; and
   determining the property of the material employing the selected set of calibration values, the property of the material being automatically determined once the measured spectral pattern is formed.

2. The method of claim 1 in which the property is thickness, the method further comprising the step of illuminating the material with infrared radiation.

3. The method of claim 2 further comprising the step of providing wavelengths of infrared radiation between about 1.3 to 3.4 microns.

4. The method of claim 1 further comprising the step of employing a spectrometer for detecting the light coming from the material and then forming the measured spectral pattern.

5. The method of claim 1 further comprising the step of reselecting a set of calibration values in predetermined circumstances.

6. The method of claim 5 further comprising the step of reselecting a set of calibration values on a periodic basis.

7. The method of claim 5 further comprising the step of reselecting a set of calibration values at a splice in the material.

8. The method of claim 5 further comprising the step of reselecting a set of calibration values when the measured spectral pattern reaches a threshold limit.

9. The method of claim 1 further comprising the step of carrying the material on a substrate.

10. The method of claim 9 further comprising the step of detecting reflected light with the detector.

11. A method of processing material in a manufacturing line comprising the steps of:
    forming the material into a continuous sheet;
    moving the material through the manufacturing line; and
    measuring a property of the moving material with a gauging system comprising:
        illuminating the material with multiple wavelengths of light;
        detecting light coming from the material with a detector;
        forming a measured spectral pattern for the material from The detected light;
        matching the measured spectral pattern with one of a plurality of spectral patterns stored in a spectral pattern library;
        selecting a set of calibration values for said one of a plurality of spectral patterns from a calibration value library; and
        determining the property of the material employing the selected calibration values.

12. The method of claim 11 further comprising the step of providing infrared radiation for illuminating the material.

13. The method of claim 11 further comprising the step of carrying the material on a substrate.

14. The method of claim 11 further comprising the step of reselecting a set of calibration values in predetermined circumstances.

15. The method of claim 14 further comprising the step of reselecting a set of calibration values on a periodic basis.

16. The method of claim 14 further comprising the step of reselecting a set of calibration values at a splice in the material.

17. The method of claim 14 further comprising the step of reselecting a set of calibration values when the measured spectral pattern reaches a threshold limit.

18. The method of claim 11 in which the property is thickness, the method further comprising the step of controlling the thickness of the material.

19. The method of claim 18 in which the material is formed by a coating process, the method further comprising the step of controlling the coating process.

20. The method of claim 18 in which the material is formed by a spraying process, the method further comprising the step of controlling the amount of material sprayed per unit time.

21. A method of controlling a manufacturing line which processes, a material formed into a continuous sheet that moves through the manufacturing line, the method comprising the steps of:
    measuring a property of the moving maternal with a gauging system, the gauging system comprising a light source for illuminating the material with multiple wavelengths of light, a detector for detecting light coming from the material and forming a measured spectral pattern for the material from the detected light, a spectral pattern library containing a plurality of spectral patterns for matching, with the measured spectral pattern, and a calibration value library containing sets of calibration values for the plurality of spectral patters, wherein a selected set of calibration values is employed for determining the property of the material; and
    controlling the processing of the material based on the measured property of the material.

22. The method of claim 21 in which the property is thickness, the method further comprising the step of controlling the thickness of the material.

23. The method of claim 22 in which the material is formed by a coating process, the method further comprising the step of controlling the coating process.

24. The method of claim 22 in which the material is formed by a spraying process, the method further comprising the step of controlling the amount of material sprayed per unit time.

25. The method of claim 21 further comprising the step of carrying the material on a substrate.

26. A gauging system for measuring a property of a moving material comprising:
    light source for illuminating the moving material with multiple a wavelengths of light;
    detector for detecting light coming from the material and forming a measured spectral pattern for the material from the detected light;
    a spectral pattern library containing a plurality of spectral patterns for matching with the measured spectral pattern;
    a calibration value library containing sets of calibration values for the plurality of spectral patterns, wherein a selected set of calibration values is employed for determining the property of the material, the property of the material being automatically determined once the measured spectral pattern is formed.

27. The gauging system of claim 26 in which the property is thickness and the light source provides infrared radiation.

28. The gauging system of claim 27 in which the infrared radiation has wavelengths between about 1.3 to 3.4 microns.

29. The gauging system of claim 26 further comprising a spectrometer for detecting light coming from the material and then forming the measured spectral pattern.

30. The gauging system of claim 26 in which the material is carried on a substrate.

31. A manufacturing line for processing a material comprising:
    means for forming the material into a continuous sheet of material which moves through the manufacturing line; and
    a gauging system for measuring a proper of the moving material, the gauging system comprising a light source for illuminating the material with multiple wavelengths of light, a detector for detecting light coming from the material and forming a measured spectral pattern for the material from the detected light, a spectral pattern library containing a plurality of spectral patterns for matching with the measured spectral pattern, and a calibration value library containing sets of calibration values for the plurality of spectral patterns, wherein a selected set of calibration values is employed for determining the property of the material.

32. The manufacturing line of claim 31 in which the property is thickness and the light source provides infrared radiation.

33. The manufacturing line of claim 31 further comprising a spectrometer for detecting light coming from the material and then forming the measured spectral pattern.

34. The manufacturing line of claim 31 in which the material is carried on a substrate.

35. The manufacturing line of claim 31 in which the material is formed by a coating process.

36. The manufacturing line of claim 31 in which the material is formed by a spraying process.

37. A control system for a manufacturing line which processes a material formed into a continuous sheet that moves through the manufacturing line, the control system comprising:

a gauging system for measuring property of the moving material comprising a light source for illuminating the material with multiple wavelengths of light, a detector for detecting light coming from the material and forming a measured spectral pattern for the material from the detected light, a spectral pattern library containing a plurality of spectral patterns for matching with the measured spectral pattern, and a calibration value library containing sets of calibration values for the plurality of spectral patterns, wherein a selected set of calibration values is employed for determining the property of the material, and means for controlling processing of the material based on the measured property of the material.

38. The control system of claim 37 in which the property is thickness and wherein the thickness of the material is controlled.

39. The control system of claim 38 in which the material is formed by a coating process, the thickness of the material being controlled by controlling the coating process.

40. The control system of claim 38 in which the material is formed by a spraying process, the thickness of the material being controlled by controlling the amount of material sprayed per unit time.

41. The control system of claim 37 in which the material is carried on a substrate.

* * * * *

UNITED STATES PATENT AND TRADEMARK OFFICE
CERTIFICATE OF CORRECTION

PATENT NO.    : 6,441,375 B1
DATED         : August 27, 2002
INVENTOR(S)   : Gareth Joseph and David F. Wood It is certified that error appears in the above-identified patent and that said Letters Patent is hereby corrected as shown below:

Column 8,
Line 61, after the semicolon ";" delete the word "and".

Column 9,
Line 39, delete "The" and insert -- the --.

Column 10,
Line 9, delete "maternal" and insert -- material -- and
Line 16, after "matching" delete the comma ",".
Line 38, before "light source" insert -- a --.
Line 39, before "wavelengths" delete "a", and
Line 40, before "detector" insert -- a --.
Line 66, delete "proper" and insert -- property --.

Column 11,
Line 27, before "property" insert -- a --.

Signed and Sealed this

Fourteenth Day of January, 2003

JAMES E. ROGAN
*Director of the United States Patent and Trademark Office*